United States Patent [19]

Kanner et al.

[11] Patent Number: 4,556,725

[45] Date of Patent: Dec. 3, 1985

[54] PROCESS FOR PREPARING TRIACETOXYSILANES FROM TRIS(AMINO)SILANES

[75] Inventors: Bernard Kanner, West Nyack; Jennifer M. Quirk, Bedford Hills; Arthur P. De Monte, Brooklyn; Steven P. Hopper, Mahopac, all of N.Y.

[73] Assignee: Union Carbide Corporation, Danbury, Conn.

[21] Appl. No.: 694,307

[22] Filed: Jan. 24, 1985

[51] Int. Cl.$^4$ ............................ C07F 7/08; C07F 7/18
[52] U.S. Cl. ..................................................... 556/442
[58] Field of Search ........................................ 556/442

[56] References Cited

U.S. PATENT DOCUMENTS

| | | | |
|---|---|---|---|
| 2,623,832 | 12/1952 | MacKenzie et al. | 106/287 |
| 2,634,285 | 4/1953 | Rust et al. | 556/442 |
| 2,866,800 | 12/1958 | MacKenzie et al. | 556/442 |
| 4,176,130 | 11/1979 | John et al. | 556/442 |
| 4,360,686 | 11/1982 | Wang et al. | 556/442 X |

OTHER PUBLICATIONS

Miner, C. S.; Bryan, L. A.; Holysz, R. P. and Pedlow, G. W.; Industr. Eng. Chem. (Industr.) 39 (1947) 1368.
Larsson, E. Chalmers tek. Hogsk; Handl. 115 (1951) 9.

*Primary Examiner*—Paul F. Shaver
*Attorney, Agent, or Firm*—Paul W. Leuzzi, II

[57] ABSTRACT

Triacetoxysilanes are prepared by adding a tris(amino)silane to acetic anhydride and maintaining the reaction mix at a temperature no greater than about 50° C.

11 Claims, No Drawings

PROCESS FOR PREPARING TRIACETOXYSILANES FROM TRIS(AMINO)SILANES

BACKGROUND OF THE INVENTION

1. Field of the Invention

The present invention relates to a process for the preparation of triacetoxysilanes from tris(amino)silanes, and in particular, to a low temperature process for providing high yields of triacetoxysilanes from acetic anhydride and tris(amino)silanes.

2. Description of the Prior Art

Traditionally, acetoxysilanes have been prepared from the reaction of the corresponding chlorosilane ($RSiCl_3$) with acetic acid or acetic anhydride in a batch or continuous process. Acetic acid has been generally regarded as the preferred reagent in view of its lower cost and also because hydrogen chloride is the by-product of the reaction. When acetic anhydride is employed for reaction with chlorosilane, acetyl chloride is formed, in addition to the desired acetoxysilane.

It has been reported in the the literature that mono- and di-aminosilanes react with acetic acid or acetic anhydride to give the corresponding acetoxysilanes, as, for example 1. Miner, C. S.; Bryan, L. A.; Holysz, R. P. and Pedlow, G. W.; Industr. Eng. Chem. (Industr.) 39 (1947) 1368
2. Larsson, E. Chalmers tek. Hogsk; Handl. 115 (1951) 9.

However, such references do not teach that triacetoxysilanes, such as vinyl- and ethyl triacetoxysilane, can be prepared from the reactions of triaminosilanes with acetic acid or acetic anhydride. It would have been expected, in any event, that this reaction would be difficult to carry out, since amines have been shown to react with silyl acetates to give a silicon polymer and the corresponding acetamide in U.S. Pat. No. 2,623,832, issued Dec. 30, 1952.

SUMMARY OF THE INVENTION

The present invention is a process for preparing triacetoxysilanes by adding a tris(amino)silane of the general formula I:

$$R'Si(NRR'')_3 \qquad [I]$$

wherein R is a saturated or unsaturated aliphatic hydrocarbon radical or an aromatic hydrocarbon radical and R' and R'' are the same or different and each is hydrogen, a saturated or unsaturated aliphatic hydrocarbon radical or an aromatic hydrocarbon radical, to acetic anhydride to form a reaction mixture and maintaining the reaction mixture at a reaction temperature no greater than about 50° C. to form a triacetoxysilane of the general formula II:

$$R'Si(OC(O)CH_3)_3 \qquad [II]$$

In addition to the desired triacetoxysilane of formula II, an acetamide of the formula $CH_3C(O)N(RR'')$ is also formed.

In the process of the invention it is critical that the tris(amino)silane is added to the acetic anhydride at low reaction temperatures. It is believed that the acetic anhydride acts to scavenge free amine from the reaction mixture and to convert that amine to its corresponding acetamide. Since it has been reported that available amine functionality can react readily with silyl acetates to yield a silicon polymer, the reservoir of acetic anhydride reactant present is believed to selectively convert any transient amine group from the tris(amino)silane reactant to an acetamide. Therefore, the amine is not available to react with the triacetoxysilane product to produce a silicone polymer.

DESCRIPTION OF PREFERRED EMBODIMENTS

The tris(amino)silane of the invention has the general formula I as follows:

$$R'Si(NRR'')_3 \qquad [I]$$

wherein R is a saturated or unsaturated aliphatic hydrocarbon radical or an aromatic hydrocarbon radical and R' and R'' are the same or different and each is hydrogen, a saturated or unsaturated aliphatic radical or an aromatic hydrocarbon radical.

Typical examples of R, R' and R'' are alkyl radicals, such as methyl, ethyl, propyl, isopropyl, butyl, isobutyl, pentyl, isopentyl, neopentyl, hexyl, octyl, dodecyl, octadecyl, 3-methylheptyl, 6-butyloctadecyl, tertiary butyl and 2,2-diethylpentyl; alkenyl radicals, such as allyl, hexenyl, butenyl, 3-octenyl, 4,9-octadecadienyl and 4-nonenyl; alkynyl radicals, such as propynyl, heptynyl, butynyl, decynyl and alkenynyl radicals, such as 1-penten-3-ynyl and 2-ethyl-1-buten-3-ynyl; cycloaliphatic radicals, such as cyclobutyl, cyclopentyl, cyclohexyl, cycloheptyl, propylcyclohexyl, 2,4-dimethylcyclopentyl, cyclohexenyl, bicyclo(3.1.0)hexyl, tricyclo(3.2.1.1$^{3,8}$)-5-nonenyl, spiro [4.5]decyl, dispiro(4.1.4.2)-1-tridecenyl, decahydronaphthyl, 2.3-dihydroindyl and 1,2,3,4-tetrahydronaphthyl and aryl radicals, such as phenyl, tolyl, xylyl, 3-ethylphenyl, naphthyl, pentaphenyl, 3,4-methylethyl-phenyl, 2-phenyl-octyl, 3-methyl-2-(4-isopropylphenyl)heptyl, benzyl, 2-ethyl-tolyl, 2-ethyl-p-cymenyl, diphenyl-methyl, 4,5-diphenylpentyl, 4-m-terphenyl, 9,9'-bifluoryl and beta-phenylethyl.

In addition R and R'' can together form a heterocyclic radical with the nitrogen (N) of formula I, such as a piperidino, piperazino or morpholino radical or an alkyl substituted heterocyclic radical or the like.

Typical examples of the tris(amino)silanes of this invention include:
$HSi[N(CH_3)_2]_3$
$HSi[N(CH_3)(C_2H_5)]_3$;
$HSi[N(C_2H_5)_2]_3$;
$HSi[N(C_3H_7)_2]_3$;
$HSi[N(H)(CH_2CH_2CH_2CH_3)]_3$;
$HSi[N(CH_3)(C_{12}H_{25})]_3$;
$CH_3Si[N(C[CH_3]_3)_2]_3$;
$C_2H_5Si[N(CH_3)(CH_2CH=CH_2)]_3$;
$C_3H_7Si[N(CH_3)(CH_2C\equiv CCH_3)]_3$;
$CH_2=CHSi[N(CH_3)_2]_3$;
$C_4H_9Si[NH(CH_3)]_3$;

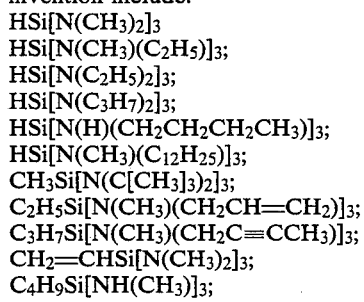

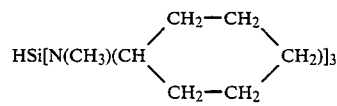

$HSi[NH(C_6H_5)]_3$;
$HSi[N(C_6H_5)_2]_3$;

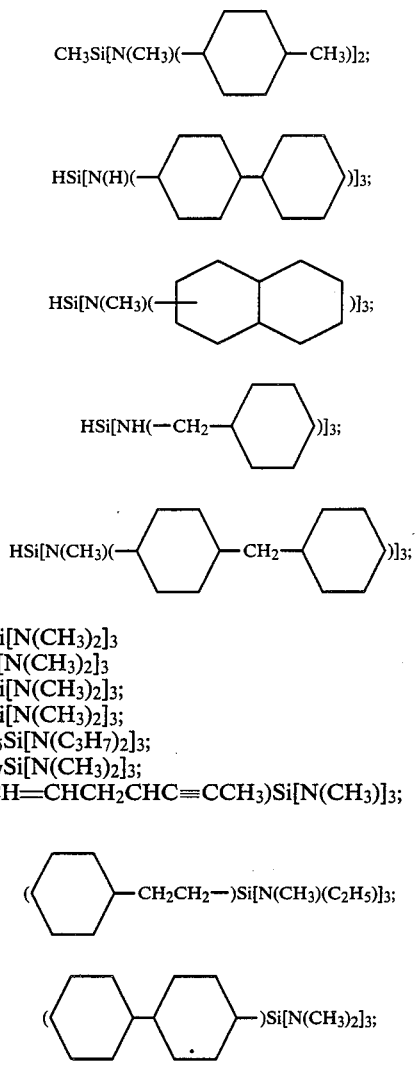

C$_2$H$_5$Si[N(CH$_3$)$_2$]$_3$
CH$_3$Si[N(CH$_3$)$_2$]$_3$
C$_2$H$_5$Si[N(CH$_3$)$_2$]$_3$;
C$_3$H$_7$Si[N(CH$_3$)$_2$]$_3$;
C$_{12}$H$_{15}$Si[N(C$_3$H$_7$)$_2$]$_3$;
C$_{13}$H$_{27}$Si[N(CH$_3$)$_2$]$_3$;
(CH$_2$CH=CHCH$_2$CHC≡CCH$_3$)Si[N(CH$_3$)]$_3$;

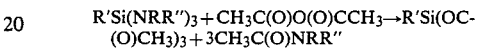

CH$_3$CH=CHSi[N(CH$_3$)$_2$]$_3$.

In general the preferred aminosilanes of the invention are those in which R' is hydrogen, vinyl and lower alkyl, and R and R" are the same and are each lower alkyl.

Especially preferred tris(amino)silanes of the invention include: vinyltris(dimethylamino)silane, ethyltris(dimethylamino)silane, methyltris(dimethylamino)silane and tris(dimethylamino)silane.

The second reactant of the invention is acetic anhydride. For most purposes acetic anhydride is added directly to the reaction. The acetic anhydride reactant, however, may be formed in situ, if desired, prior to the reaction.

The molar ratio of tris(amino)silane reactant to acetic anhydride reactant is preferably no greater than about 1:3, which is the stoichiometric ratio for complete reaction. If desired, an excess of acetic anhydride can be employed. If an excess of tris(amino)silane is utilized, the reaction will proceed, but will result in reduced amounts of triacetoxysilane, and increased amounts of undesired by-products.

The reaction should be conducted at a temperature no greater than about 50° C. At reaction temperatures greater than about 50° C., the yield of desired triacetoxysilane is significantly reduced and undesired by-products are found in increasing amounts. Better results are obtained if the reaction temperature is maintained at no greater than about (—)20° C. The lower reaction temperature is not critical, provided that the reaction mixture remains homogeneous. For best results, it is particularly preferred to conduct the reaction at temperatures between about −20° C. and 0° C.

The order of addition of reactants to the process is critical. It is necessary to add the tris(amino)silane of the invention to the acetic anhydride reactant for satisfactory acetoxylation. Should the order of addition be reversed, a silicon polymer is formed and the single liquid product is an acetamide.

The equation for the process of the invention is as follows:

$$R'Si(NRR'')_3 + CH_3C(O)O(O)CCH_3 \rightarrow R'Si(OC(O)CH_3)_3 + 3CH_3C(O)NRR''$$

Accordingly, in addition to the triacetoxysilane of the invention, an acetamide is also formed corresponding to the amino group in the aminosilane reactant.

If the order of addition is reversed or if an excess of tris(amino)silane were present, it is believed that the amino functionality, available from the tris(amino)silane, reacts with the triacetoxysilane product to yield the corresponding acetamide and a silicon polymer in accordance with the following equation:

$$R'Si(NRR'')_3 + R'Si(OC(O)CH_3)_3 \rightarrow 3CH_3C(O)NRR'' + (R'SiO_n)$$

The reaction time is not a significant factor in the process. In general, the reaction is completed in from about ½ to 6 hours, and, usually, in from about 2 to 3 hours. The reaction pressure is not a critical factor in the process. The reaction can be carried out at atmospheric, subatmospheric or superatmospheric pressure.

The reaction may be carried out in the absence or presence of a reaction solvent. If it is desired to enhance the solubility of the reactants or to provide a heat sink to help maintain proper temperature control, a solvent can be employed. Typical reaction solvents include hydrocarbon solvents, such as octane, xylene or, preferably, triisopropylbenzene.

The following examples illustrate certain preferred embodiments of the invention under laboratory conditions and are not intended to be limitative of scope.

EXAMPLE 1

A 50 ml three necked round bottom flask was equipped with a stirring bar, thermometer, addition funnel and reflux condenser topped with a nitrogen inlet tube. The flask was charged with 12.0 g (0.12 mole) of acetic anhydride. To the dropping funnel was added 6.8 g (0.036 mole) of ethyltris(dimethylamino)silane. The ethyltris(dimethylamino)silane was added dropwise to the acetic anhydride, which had been pre-cooled to 0° C., over a period of two hours, with the temperature of the reaction mixture never being allowed to exceed 20° C. The yield of ethyltriacetoxysilane was determined to be 85% by GC area percent. The material was then distilled under vacuum (74°–75° C./0.7 mm Hg) and showed no evidence of decomposition.

EXAMPLE 2

The experimental procedure followed was identical to that of Example 1, except that vinyltris(dimethylamino)silane was used as the starting silane. The yield of vinyltriacetoxysilane was 85% by GC area percent and the material was then distilled under vacuum (74° C./0.7 mm Hg) without any signs of decomposition.

EXAMPLE 3

The experimental procedure employed was identical to that of Example 1, except methyltris(dimethylamino)silane was used as the starting silane. The yield of methyltriacetoxysilane was 80% by GC area percent and the material was then distilled under vacuum (65° C./0.7 mm Hg) without any sign of decomposition.

EXAMPLE 4

A 50 ml three necked round bottom flask was equipped with a stirring bar, thermometer, addition funnel and reflux condenser topped with a nitrogen inlet tube. The flask was charged with 3.0 g (0.03 mole) of acetic anhydride. The acetic anhydride reactant was then cooled to $-20°$ C. To a dropping funnel was added 1.6 g (0.01 mole) of tris(dimethylamino)silane, which was then added dropwise to the acetic anhydride over a period of 2-3 hours with the reaction temperature never being allowed to go above 0° C. The yield of triacetoxysilane was determined to be greater than 70% by GC area percent. On standing at room temperature it was noted that the triacetoxysilane exhibited a tendency to disproportionate to tetraacetoxysilane and diacetoxysilane.

COMPARATIVE EXAMPLE 1

A 50 ml three necked round bottom flask was equipped with a stirring bar, thermometer, addition funnel and reflux condenser topped with a nitrogen inlet tube. The flask was charged with 3.0 g (0.017 mole) of methyltris(dimethylamino)silane and cooled to 0° C. in an ice bath. A dropping funnel was charged with 5.2 g (0.051 mole) of acetic anhydride which was then added dropwise to the aminosilane over a period of 2-3 hours with the temperature never being allowed to exceed 20° C. A GC of the reaction mixture showed the presence of unreacted acetic anhydride and N,N-dimethyl-acetamide. No silicon containing products were found by G.C.

The results demonstrate the criticality of adding the aminosilane to the acetic anhydride.

COMPARATIVE EXAMPLE 2

The reaction was run as described in Comparative Example 2, except that ethyltris(dimethylamino)silane was used as the starting silane and triisopropylbenzene was used as a solvent. The reaction was run at room temperature. No silicon containing products were found by GC.

EXAMPLE 5

The reaction was run in accordance with the procedure of Example 1, employing as a solvent, triisopropylbenzene (5.3 g). During the course of the addition of ethyltris(dimethylamino)silane to the acetic anhydride the reaction temperature was never allowed to exceed 50° C. A GC of the reaction mixture after the addition was completed showed that ethyltriacetoxysilane had been formed in approximately 70% yield.

What is claimed is:

1. Process for preparing triacetoxysilanes comprising:
   (a) adding a tris(amino)silane of the general formula[I]:

$$R'Si(NRR'')_3 \qquad [I]$$

wherein R is a saturated or unsaturated aliphatic hydrocarbon radical or an aromatic hydrocarbon radical and R' and R" are the same or different and each is hydrogen, a saturated or unsaturated aliphatic hydrocarbon radical, or an aromatic hydrocarbon radical to acetic anhydride to form a reaction mixture; and
   (b) maintaining the reaction mixture at a reaction temperature no greater than about 50° C. to form a triacetoxysilane of the general formula [II]:

$$R'Si(OC(O)CH_3)_3 \qquad [II]$$

wherein R' is as before.

2. The process of claim 1 in which R' is hydrogen, vinyl or lower alkyl and R and R" are the same and each is lower alkyl.

3. The process of claim 1 in which the tris(amino)silane is vinyltris(dimethylamino)silane.

4. The process of claim 1 which the tris(amino)silane is ethyltris(dimethylamino)silane.

5. The process of claim 1 in which the tris(amino)silane is methyltris(dimethylamino)silane.

6. The process of claim 1 in which the tris(amino)silane is tris(dimethylamino)silane.

7. The process of claim 1 in which the molar ratio of the tris(amino)silane to the acetic anhydride is no greater than about 1:3.

8. The process of claim 1 in which the reaction temperature is maintained at no greater than about $-20°$ C.

9. The process of claim 1 in which the reaction temperature is maintained between about $-20°$ and 0° C.

10. The process of claim 1 in which the reaction is carried out in a hydrocarbon solvent.

11. The process of claim 10 in which the hydrocarbon solvent is triisopropylbenzene.

* * * * *